United States Patent [19]
Bacotti et al.

[11] 4,129,361
[45] Dec. 12, 1978

[54] EYE TESTING DEVICE FOR PRESCRIBING EYEGLASSES

[76] Inventors: Peter A. Bacotti, 53 Eighth Ave., Brooklyn, N.Y. 11217; Frederick M. Kraft, 25 Central Park West, New York, N.Y. 10023

[21] Appl. No.: 776,182

[22] Filed: Mar. 10, 1977

[51] Int. Cl.² .......................... A61B 3/04; A61B 3/02; G02C 7/02; G02C 5/00
[52] U.S. Cl. ...................................... 351/22; 351/26; 351/167; 351/154
[58] Field of Search ...................... 351/22, 19, 26, 167, 351/154; 350/189

[56] References Cited
U.S. PATENT DOCUMENTS
3,169,247  2/1965  Davis et al. .................. 351/167
FOREIGN PATENT DOCUMENTS
457978  12/1936  United Kingdom .................. 351/22

*Primary Examiner*—Paul A. Sacher
*Assistant Examiner*—Rodney B. Bovernick
*Attorney, Agent, or Firm*—Erwin Koppel

[57] ABSTRACT

A device for determining a prescription lens for eyeglasses to be used by highly hyperopic patients, in which a frame mounted lens is inserted in a trial lens mounting to project on either side of the frame with one surface of the lens formed with an aspherical convex curvature and the other surface of the lens being concave and formed with a spherical curvature.

3 Claims, 12 Drawing Figures

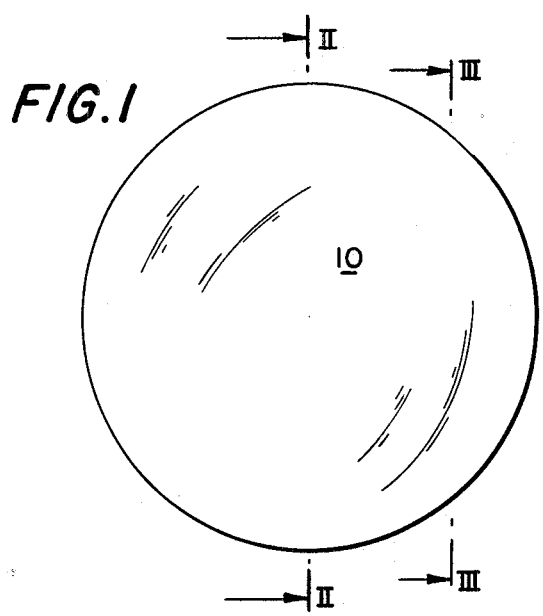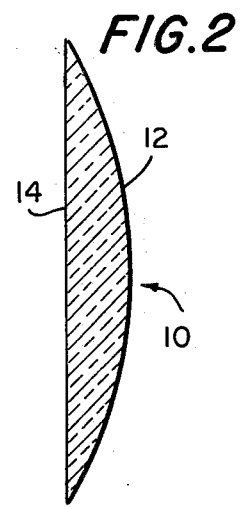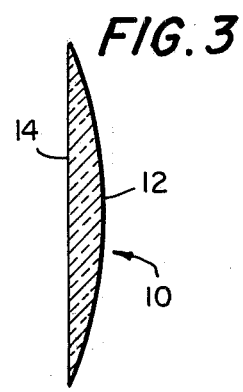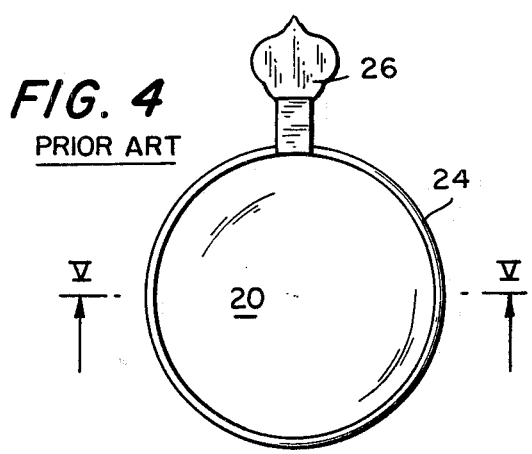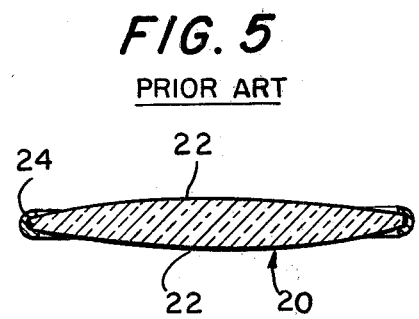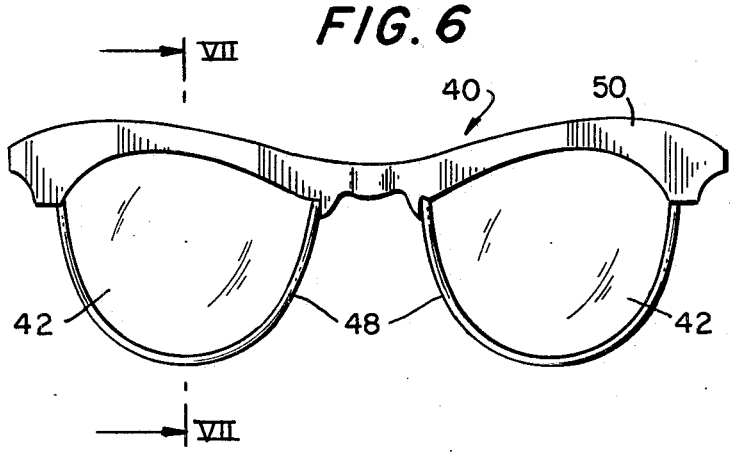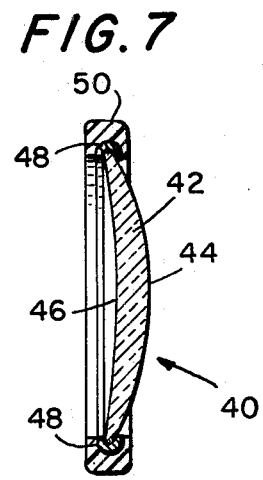

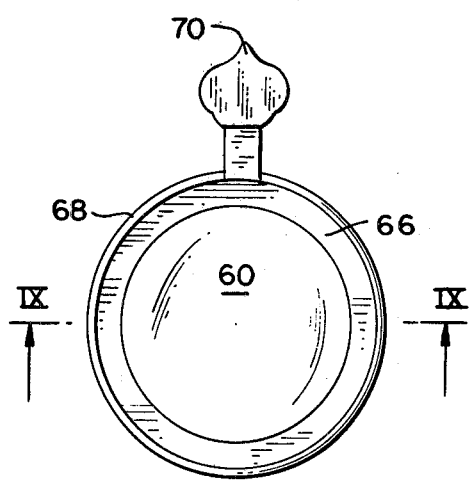
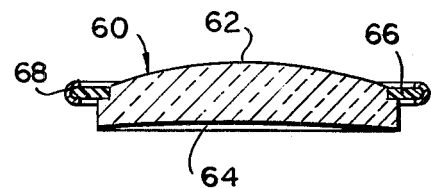
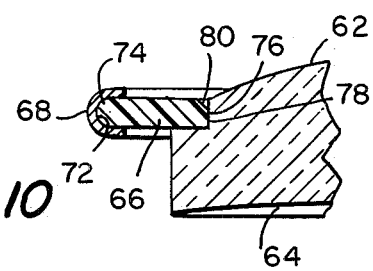
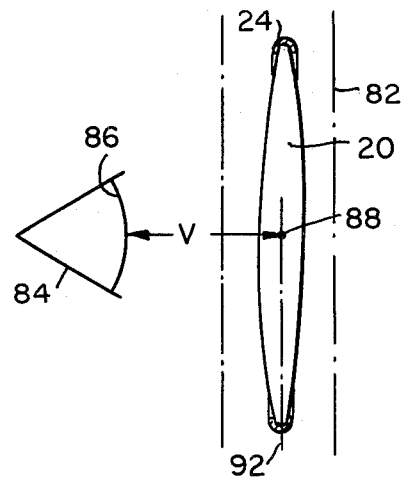
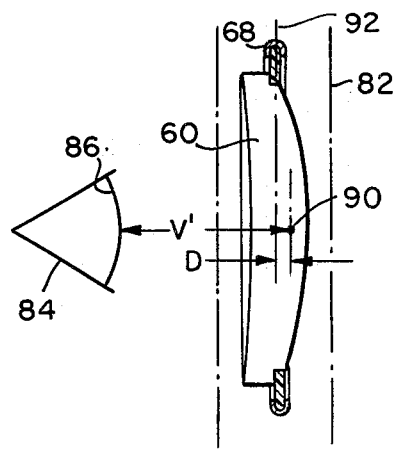

EYE TESTING DEVICE FOR PRESCRIBING EYEGLASSES

This invention relates to an eye testing device for determining prescription lenses for eyeglasses used by highly hyperopic patients, and it is particularly concerned with providing a testing lens closely approximating the actual lens of the eyeglasses.

In prescribing lenses for eyeglasses, it is the conventional practice of the optometrist or ophthalmologist to utilize test lenses of different diopter powers. These are furnished to the optometrist by lens manufacturers, and they are provided in the form of cylindrical and spherical lenses each mounted in a frame having a tab for handling. In prescribing for the patient a trial lens mounting is placed on or adjacent the head of the patient, so that the testing lens can be inserted therein for the patient to look through for correction. For patients who require a minor correction, the use of testing lenses as described above is generally satisfactory. However, for highly hyperopic patients, such as patients who have had a cataract operation, the use of this conventional testing lens creates errors in the data prescription obtained. This is due to the fact that the highly hyperopic patient requires an aspherical lens of high diopter power with different curvature and vertex characteristics as compared to the conventional testing lens. Accordingly, it is clear that using a spherical lens for testing highly hyperopic patients will give inaccurate data, and this will necessitate later trial and error techniques to grind and fit the final aspherical lenses.

From the above it is clear that there is a need for a testing lens that more closely approximates the type of lens required for a highly hyperopic patient, and it is an object of the present invention to provide such improved testing lens.

It is a further object of the present invention to provide a testing lens including an aspherical surface closely approximating the aspherical curvature of the lens fitted into the eyeglasses.

It is still another object of the present invention to provide a testing lens mounted in a frame to extend on either side thereof and provide a vertex distance to the eye of the patient closely approximating the vertex distance of the final eyeglass lens.

It is a still further object of the present invention to provide a method of manufacturing a test lens in which a blank is ground with an aspherical surface having a diopter power of at least +10.

It is a still further object of the present invention to provide a method of manufacturing a test lens for highly hyperopic patients comprising the mounting of a lens having an aspherical surface within a frame by means of a snap fit.

Additional objects not specifically set forth will be apparent from the following detailed description of the present invention.

Referring to the drawings:

FIG. 1 shows a front view of a glass blank that is to be ground into a lens;

FIG. 2 shows a section taken along the line II—II of FIG. 1;

FIG. 3 shows a section taken along line III—III of FIG. 1;

FIG. 4 is a front view of a conventional testing lens;

FIG. 5 is a sectional view taken along lines V—V of FIG. 4;

FIG. 6 is a front view of a pair of eyeglasses used by a highly hyperopic patient;

FIG. 7 is a sectional view taken along line VII—VII of FIG. 6;

FIG. 8 is a front view of the novel eye testing lens of the present invention;

FIG. 9 is a sectional view taken along line IX—IX of FIG. 8;

FIG. 10 is an enlargement of the section of FIG. 9 to show the mounting of the lens in the frame;

FIG. 11 illustrates the use of a conventional testing lens inserted in a trial lens mounting shown in schematic form; and FIG. 12 is a view similar to FIG. 11 showing the use of the novel testing lens of the present invention.

FIGS. 1 to 3 show a glass blank before it is ground into a testing lens or final lens, and it is seen that the blank 10 has a large curvature 12 on one side and a substantially flat surface 14 on the other side with a generally circular overall shape. It has been conventional for optometrists and ophthalmologists to be furnished with testing lenses formed from these blanks by grinding the blanks to have specific diopter powers with opposing spherical curvatures as shown in FIGS. 4 and 5.

FIGS. 4 and 5 illustrate a conventional testing lens, and it will be seen that this lens 20 is circular in shape and includes oppositely facing surfaces 22 having the same convex spherical curvature. This conventional testing lens is mounted in a frame 24 having a grasping tab 26 to provide for handling and insertion into a trial lens mounting unit 82 as shown in FIGS. 11 and 12 to be described hereinafter.

FIGS. 6 and 7 illustrate the type of eyeglasses worn by highly hyperopic patients, in which the diopter power is in the range of +10 to +12. Eyeglasses 40, shown in FIG. 6, include lenses 42 each having a convex aspherical curvature 44 of the front surface, as most clearly shown in FIG. 7. The rear surface 46 is a slightly concave spherical surface, but it will be appreciated from comparing FIGS. 5 and 7 that a considerably different type of lens is worn by the highly hyperopic patient as compared to the conventional testing lens. Each lens 42 may be mounted in its own frame 48 which is then mounted within the larger eyeglass frame 50. For this type of patient the aspherical lens 42, which conventionally includes a number of different curvatures in surface 44, is necessary to provide a larger range of focus points on the retina of the eye, and it is well known that this will not be provided by a spherical lens.

In FIGS. 8 to 10 an embodiment of the novel testing lens is shown, and this testing lens 60 would be formed by grinding blank 10 down to the desired size, which in the embodiment shown would be about 25 mm. in diameter with a convex aspherical curvature on front surface 62 and a slightly concave spherical curvature on rear surface 64. The aspherical curvature is formed by well known conventional molding, and the testing lens of this invention should have a diopter power of at least +10. In this respect it has been found sufficient for patients of the highly hyperopic type to utilize diopter powers in the range of +10 to +12 for the testing lenses.

Lens 60 is mounted in a frame. This can be a frame similar to the showing in FIGS. 4 and 5, or it can be a combination washer and frame embodiment as shown in FIGS. 8 to 10. In this embodiment washer 66 is fitted into a frame 68 having a tab 70 to use in handling and insertion into a test unit. Lens 60, washer 66 and frame 68 are generally circular in form. Washer 66 may be formed of plastic, and frame 68 may be formed of metal. Frame 68 has a convex inner surface 72 to receive convex outer surface 74 of washer 66, as shown in FIG. 10. Inner surface 76 of washer 66 is sized to form a snap fit with a notched area 78 of lens 60, and notched area 78 receives washer 66 so that lens 60 projects substantially equally on either side of frame 68. A bevel 80 is formed on the front part of surface 76.

From the above, it is clear that a novel method also is described for manufacturing testing lenses for hyperopic patients, which involves grinding a blank to provide a lens having a diopter power of at least +10 with at least one surface having an aspherical curvature, and providing a secure mounting such as by snapping the lens into a circular frame.

FIGS. 11 and 12 illustrate the different results obtained by the novel testing lens of this invention as compared to the conventional testing lens used for highly hyperopic patients. In FIG. 11 a schematic illustration shows a trial frame unit 82 positioned with respect to a patient closely adjacent to the eye 84 having a cornea 86. When a conventional spherical curvature test lens 20 is inserted in unit 82 and a desired correction achieved, measurement V is the vertex distance between cornea 86 and focal point 88. This vertex distance is critical to provide an accurate eyeglass prescription since it should be the same as when the eyeglasses are worn. Obviously, when minor correction is involved, and the patient requires a prescription lens having spherical curvature, then the testing arrangement shown in FIG. 11 is satisfactory.

When a highly hyperopic patient is involved, the prescription will be for lenses of high diopter power having an aspherical curvature. However, the test arrangement shown in FIG. 11 will not provide an accurate prescription for such a patient, as the vertex distance V is not correct for the type of lens required as shown in FIGS. 6 and 7.

In FIG. 12 the trial frame unit 82 is the same as in FIG. 11 and is able to receive the novel testing device of this invention. Lens 60 within frame 68 is shown as inserted in trial frame unit 82, and it will be appreciated that focal point 90 of lens 60 is correctly located with respect to cornea 86 since lens 60 closely approximates the final lens that the patient will be wearing. Vertex distance V' will correspond to the vertex distance of the lenses prescribed, and the difference between distances V and V' is clearly shown by the extension of the horizontal line 92 from focal point 88 which is then seen to be spaced a distance D from focal point 90. Distance D in practice has been found to be several millimeters, and this is obviously a critical distance with respect to obtaining an accurate prescription. Using the conventional practice as shown in FIG. 11, the prescription for a highly hyperopic patient would never be accurate, and the optometrist has to subsequently use trial and error techniques during final fitting to reach the correct prescription. In contrast, using the novel test lens 60, as shown inserted in unit 82 in FIG. 12, the prescription obtained for this type of patient is quite accurate, and the final fitting is considerably easier.

It is understood that in the testing procedure, there would also be the conventional cylinder correction made for astigmatism or other minor corrections, but this does not constitute part of the invention so that it need not be described.

It is intended that there may be modification, change or substitution of elements in the foregoing description, and it is further intended that some features of the invention can be employed without a corresponding use of other features. Accordingly, it is appropriate that the appended claims be construed broadly and in a manner consistent with the spirit and scope of the invention herein.

What we claim is:

1. Device for prescribing refraction lenses for eyeglasses to be used by highly hyperopic patients comprising
   a frame means:
   a testing lens mounted within said frame means:
   said lens having a first surface with a predetermined concave spherical curvature;
   said lens having a second surface spaced from said first surface and formed with an aspherical convex curvature, the curvature of said convex surface being greater than the curvature of said concave surface;
   said frame means comprising an outer circular frame having an inner circular surface and an inner circular washer having an outer circular surface that abuts said inner circular frame surface and formed to be held therein, said washer having an inner peripheral surface which includes an innermost edge having part thereof formed with an outwardly directed beveled area; and
   said lens having a first circular part which includes said concave spherical surface, said first circular part having a diameter greater than the diameter of said innermost edge of said washer, and said lens having a second circular part which includes said convex aspherical surface, said second circular part having a diameter formed to correspond with and snugly fit against said innermost edge.

2. Device according to claim 1 wherein said lens has a diopter power of at least +10 and is approximately 25 mm. in diameter.

3. Device according to claim 1 wherein said frame is positionable in a trial frame unit mounted on a patient to provide a vertex distance between the eye of the patient and said lens closely approximating the vertex distance of the eye and the lens in the prescribed eyeglasses.

* * * * *